(12) United States Patent
Bin Saleh

(10) Patent No.: US 10,335,022 B1
(45) Date of Patent: Jul. 2, 2019

(54) EAR-MOUNTED DENTAL MIRROR SUPPORT

(71) Applicant: KING SAUD UNIVERSITY, Riyadh (SA)

(72) Inventor: Eman Mohammed Saad Bin Saleh, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/124,125

(22) Filed: Sep. 6, 2018

(51) Int. Cl.
*A61B 1/247* (2006.01)
*A61C 5/82* (2017.01)
*A45D 42/12* (2006.01)

(52) U.S. Cl.
CPC .............. *A61B 1/247* (2013.01); *A45D 42/12* (2013.01); *A61C 5/82* (2017.02)

(58) Field of Classification Search
CPC .......... A61B 1/247; A61C 5/82; A45D 42/12; G02B 7/002
See application file for complete search history.

(56) References Cited

U.S. PATENT DOCUMENTS

| | | | | |
|---|---|---|---|---|
| 1,397,090 | A * | 11/1921 | Dimas ...................... | A61B 1/24 433/30 |
| 2,256,491 | A * | 9/1941 | Peck ........................ | A61B 3/04 33/200 |
| 2,389,428 | A * | 11/1945 | Glasser ................... | G02B 7/002 351/118 |
| 2,606,479 | A * | 8/1952 | Howe ..................... | A45D 42/12 2/DIG. 8 |
| 3,609,015 | A * | 9/1971 | Messinger ............. | A45D 42/00 248/467 |
| 3,988,058 | A | 10/1976 | Chaney | |
| 4,405,302 | A | 9/1983 | Lewis | |
| 5,458,486 | A | 10/1995 | Ballard | |
| 2008/0307560 | A1* | 12/2008 | Bellington ............. | A45D 42/12 2/174 |

* cited by examiner

*Primary Examiner* — Heidi M Eide
(74) *Attorney, Agent, or Firm* — Richard C. Litman

(57) ABSTRACT

The ear-mounted dental mirror support includes two arms, each having a hooked end configured to wrap around the back of an ear. The arms are connected to a cross-member at the end opposite the hook. A multi-rod adjustment member is pivotally attached to the cross-member. A mirror is pivotally attached to the free end of the adjustment member. The device is designed to be secured to a patient's ears by the arms with the cross-member resting on the patient's chin. The mirror can be adjusted to reflect different portions of the patient's mouth to help a person applying treatment visualize the treatment zone. The arms and cross-member may include projections to assist in securing a dental dam in place around the patient's mouth.

4 Claims, 4 Drawing Sheets

EAR-MOUNTED DENTAL MIRROR SUPPORT

BACKGROUND

1. Field

The disclosure of the present patent application relates to dental instruments, and particularly to an ear-mounted dental mirror support for supporting a dental mirror on the patient's ears, thus freeing the dentist's hands.

2. Description of the Related Art

The oral cavity is an extremely difficult area in which to work. Vision and access are impaired by the lips, cheek, tongue, and the patient's ability to open the mouth. Restorative care must be accomplished with extreme care to avoid injuring the soft tissue structures. A dental mirror is commonly used to provide visual access and illumination to portions of the mouth. A dental mirror also gives a user the ability to see multiple different areas of the patient's mouth without having to contort their body, thus preventing unnecessary strain.

The dental mirror takes on its most important functions when it is used for indirect vision. Indirect vision is the viewing of the surgical field through the mirror image of the field. Different from the direct vision system, in indirect vision both the operatory light as well as the dental unit light are hopefully being captured by the dental mirror in such a way that the mirror may be angulated or deflected to illuminate the surgical field. While this is being achieved, the dentist or hygienist is positioning the mirror to have proper visual image of the site through the mirror.

Conventionally, the dentist accomplishes the above by a fixed handle connection to a circular mirror head pre-set at thirty to forty degrees. To use the mirror, the dentist held a working tool, such as a drill, in one hand and the mirror in the other hand. Thus, both hands were occupied, and if another tool is needed, the first tool had to be set down before the second tool could be picked up. One can see that the dentist is limited to using one tool at a time.

As the art of dentistry progressed, the dentist discovered that in some cases, he/she could perform a better job if he/she could use two working tools at the same time instead of having one hand tied to a dormant device, such as the mirror, which is only an aid to the dentist in performing his duties. In such situations, some dentists summon an assistant to help them. However, this is undesirable, because too many hands would be located within the region of the mouth.

Thus, an ear-mounted dental mirror support solving the aforementioned problems is desired.

SUMMARY

The ear-mounted dental mirror support includes two arms, each having a curled end configured to wrap around the back of an ear. The arms are connected to a cross-member at the end opposite the curl. A multi-rod adjustment member is pivotally attached to the cross-member. A mirror is pivotally attached to the free end of the adjustment member. The device is designed to be secured to a patient's ears by the arms with the cross-member resting on the patient's chin. The mirror can be adjusted to reflect different portions of the patient's mouth to help a person applying treatment visualize the treatment zone. The arms and cross-member may include projections to assist in securing a dental dam in place around the patient's mouth.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
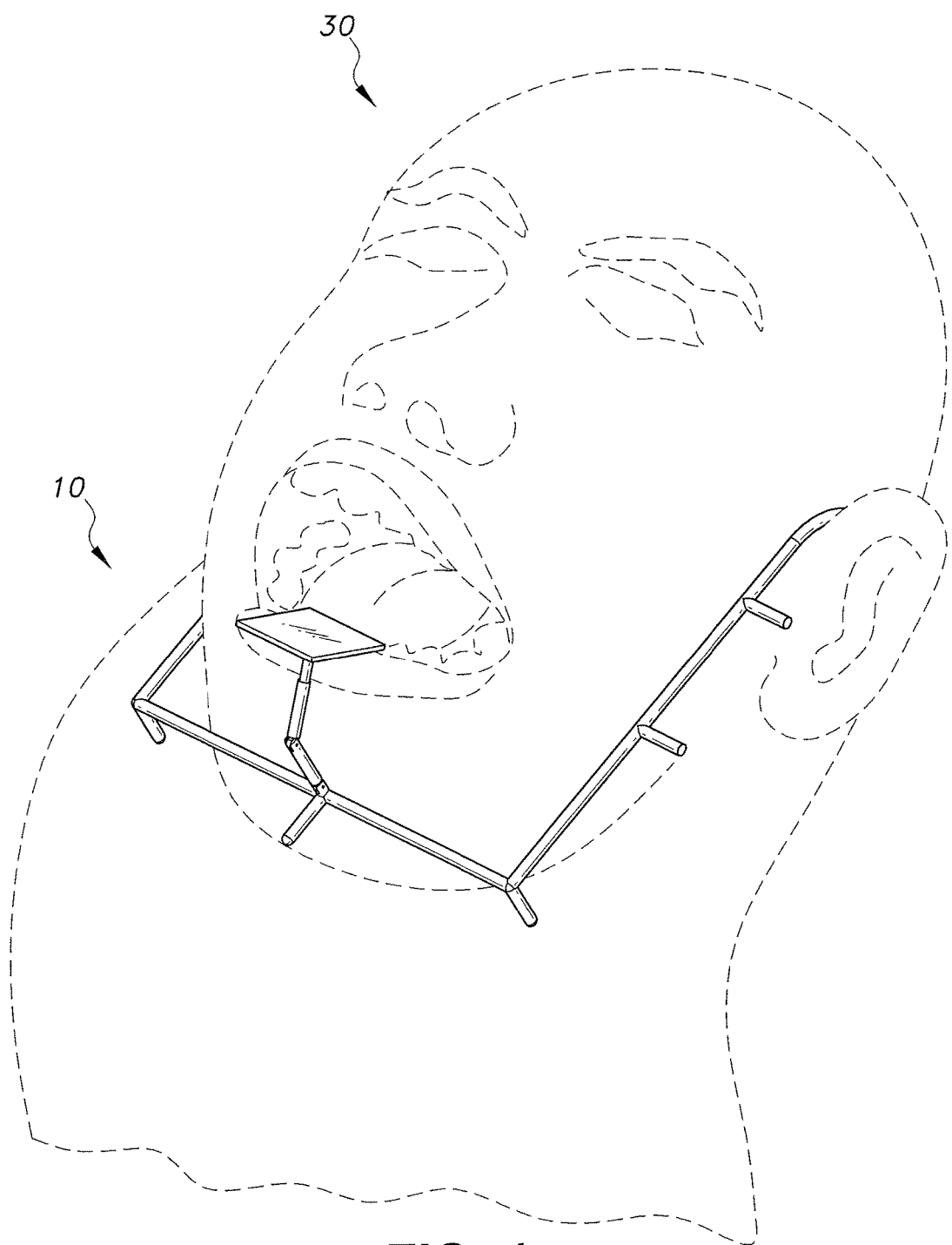
FIG. 1 is an environmental, perspective view of an ear-mounted dental mirror support.

The ear-mounted dental mirror support 10, shown in FIG. 1, includes a frame designed to hook onto a patient's 30 ears. The frame extends down to the patient's chin, where a mirror is attached immediately below the patient's mouth. The mirror is attached to the frame by pivotal supports that allow a user to adjust the angle of the mirror based on the portion of the patient's mouth the user would like to see. The frame includes projections that may be used to hold a rubber dental dam in place around the patient's mouth.

Figure 2:
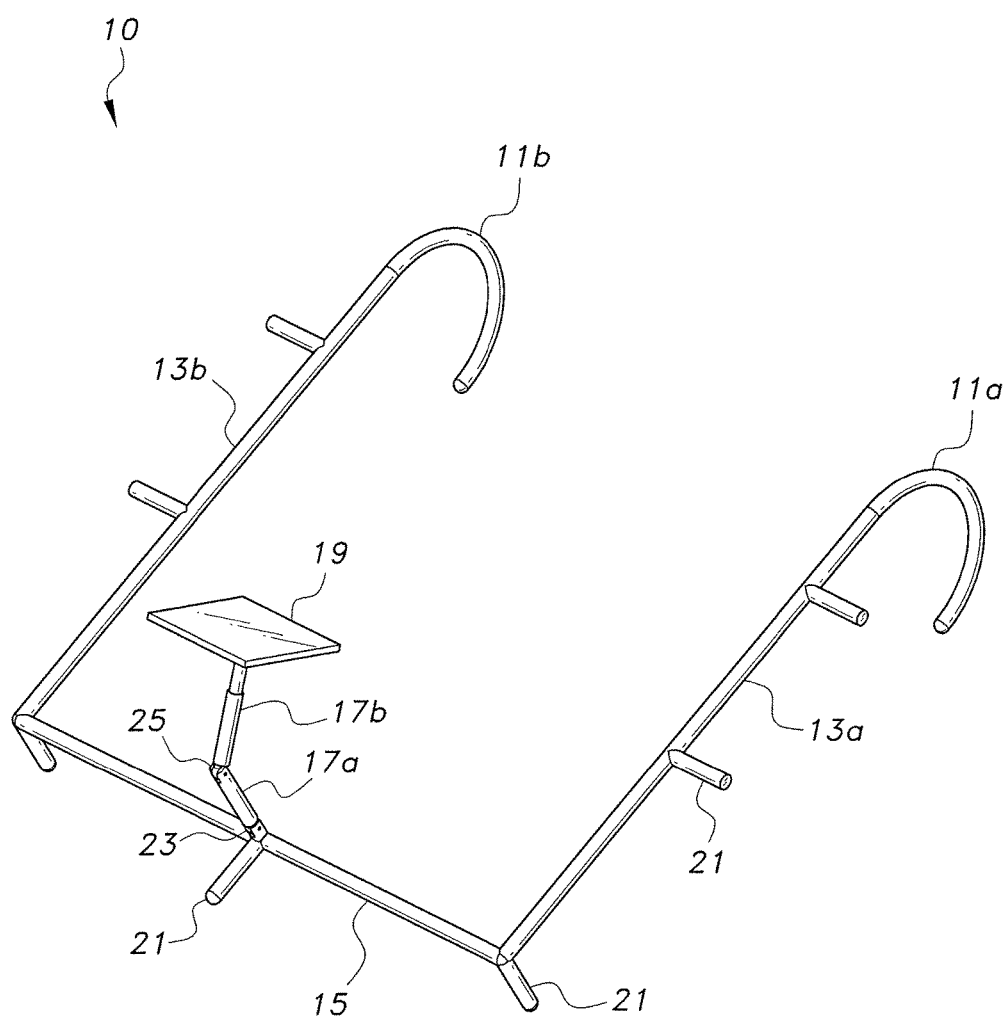
FIG. 2 is a perspective view of the ear-mounted dental mirror support of FIG. 1.

FIG. 2 details the elements of the mirror support 10. The mirror support 10 includes a left arm 13a and a right arm 13b. Each arm has a respective ear hook 11a, 11b. As shown in FIG. 2, the ear hook 11a, 11b is an arcuate portion of the arm 13a, 13b that is intended to wrap around the back of the patient's ear. Other ear engagement portions known for use on glasses are also contemplated. Additionally, a high friction coating or material, such as rubber or silicone, may be used on the ear pieces for additional securement.

The arms 13a, 13b extend from the ear hooks 11a, 11b to a cross-member 15 with the arms 13a, 13b in a parallel orientation, each arm 13a, 13b connecting to the cross-member at a right angle. It is contemplated that each of the arms 13a, 13b and the cross-member 15 have adjustable lengths to fit patients of different sizes, or for operations on different parts of the mouth that require different mirror locations. Length adjustability may be achieved by the use of telescopic members. The arms 13a, 13b and the cross-member 15 may each have an inner member and an outer member that have a slidable relation to one another. This will allow a treatment provider to set the device on a patient and easily adjust the length of each portion until the device rests on the patient in a position deemed most fit by the treatment provider. It is contemplated that the arms 13a, 13b may be connected to the cross-member 15 by hinges, allowing them to fold inward, similar to a pair of glasses. The cross member 15 may include an element on its lower side that conforms to the typical contours of a patient's chin for added stability and comfort.

The arms 13a, 13b and the cross-member 15 preferably have a length between three inches and nine inches. They may be made out of any material having adequate structural integrity to hold the mirror and a dental damn without bending. Exemplary materials include aluminum, stainless steel, titanium, polyethylene, and polyvinyl chloride.

Multiple projections 21 may extend out from the arms 13a, 13b, and cross-member 15 to hold a dental damn in place. Dental dams are used to isolate the area being worked on from the remainder of the mouth. It is necessary to retain the outer edges of the dam to keep the working area easily accessible. Dental dams are made of flexible, elastic material, and therefore can be stretched and hooked around the projections 21. The tension caused by the stretching and the friction of the material holds the dam in place on the projections 21. High friction material may be added to the projections that help prevent the dam from sliding off. In the embodiment shown in FIG. 2, the projections 21 extend out from the frame at different angles. The projections on the arms 13a, 13b and in the middle of the cross-member 15 extend horizontally out from the device, since these areas will be adjacent the face. The projections 21 at the corners connecting the arms 13a, 13b and cross-member 15 extend vertically downward, since they will be located at the sides of the chin. The downward angle of the projections may create a more usable working space for the treatment provider, since they displace the dam downward. However, different procedures may benefit from different dental dam configurations. Thus, it is contemplated that projections may extend out from the frame at angles other than the angles shown in the drawings. It is also contemplated to attach the projections 21 to the arms 13a, 13b and cross-member 15 by locking pivots so that the user can customize the orientation of the projections 21 for each procedure.

Figure 3:
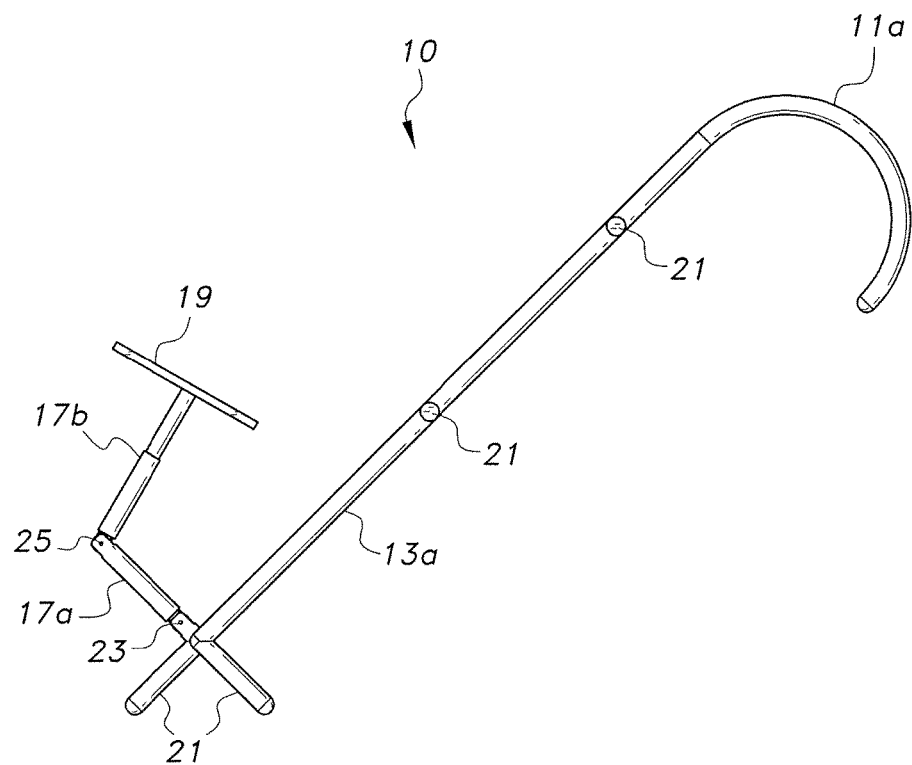
FIG. 3 is a side view of the ear-mounted dental mirror support of FIG. 1.
Figure 4:
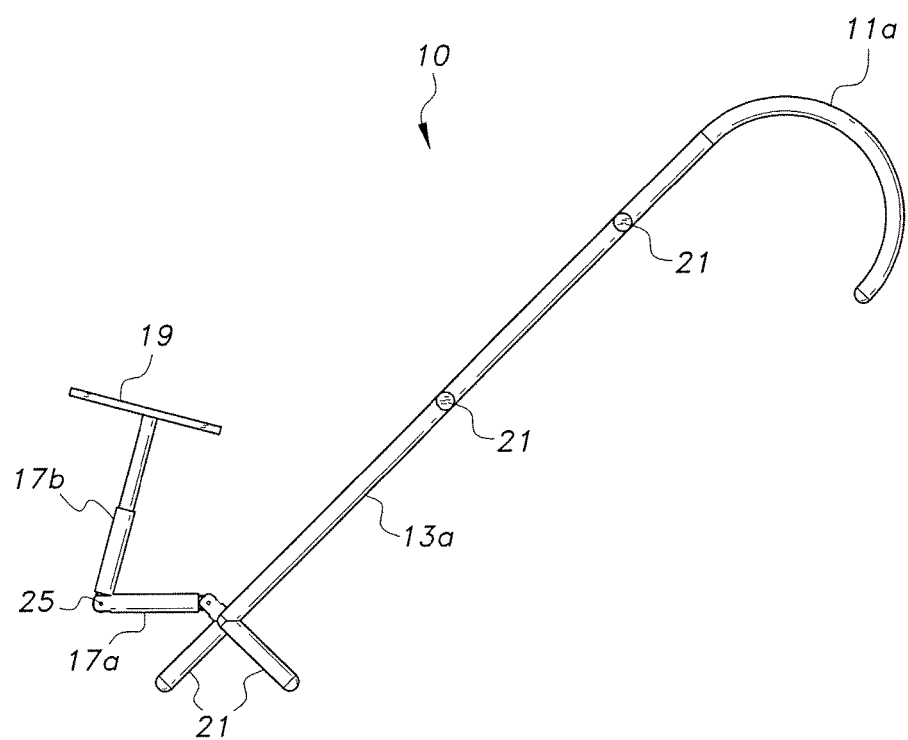
FIG. 4 is a side view of the ear-mounted dental mirror of FIG. 1, shown with the mirror support arm pivoted downward.

A mirror 19 is pivotally attached to the center of the cross-member 15 by an adjustment member. The adjustment member is pivotally attached to the cross-member 15 and also pivotally attached to the mirror 19. As shown in FIGS. 2-4, the adjustment member may comprise multiple pivotally connected rods 17a, 17b. Increasing the amount of rods in the adjustment member increases the adjustability by adding additional ranges of freedom. The embodiment shown in the Figures includes an adjustment member having two rods. However, it is contemplated to use a member having one rod or more than two pivotally connected rods. In some embodiments, a flexible gooseneck, also known as "stay-put" or "obedient tubing", may be used as the adjustable member.

When working on different areas of the mouth, a treatment provider may need the mirror 19 in different positions for provide reflections to different portions of the patient's mouth. The mirror may also need to be adjusted to look at specific location from different angles. Therefore, increasing freedom of movement will increase the user's ability to adjust the mirror 19 to the desired location and orientation. In a preferred embodiment, each of the joints connecting the mirror 19 to the cross-member 15, which includes the joint 23 connecting the adjustment member to the cross-member, the joint 25 between rods of the adjustment member connecting the adjustment member to the mirror, are all individually adjustable ball joints. Ball joints allow for adjustment in every direction, and therefore allow for maximum freedom of movement. In other embodiments, the joints 23 and 25 may each comprise two perpendicularly oriented single axis hinges. Alternatively, each joint may be a different type of joint. For example, the joint 25 between the rods 17a, 17b may be single-axis joints, while the joint 23 connected to the mirror and to the cross-member are multi-axis joints. It is further contemplated that the rods 17a, 17b of the adjustment member have telescopic abilities to further increase adjustability of the mirror position. Some embodiments of the device may include a magnifying mirror or a mirror where a portion of the mirror magnified. Some embodiments of the device may further include a light connected to the mirror 19 for assisting in illuminating the mouth.

It is contemplated that some embodiments may include position markings for the adjustable components. This will allow a user to set the device to exact position for repeat patients or certain procedures where an exact setup may be beneficial. For example, the telescopic portions may have markings spaced apart by one millimeter with a numeral every five millimeters. The pivots may have marking for every five degrees of rotation, with associated numerals to indicate the degrees. Some embodiments may include locking mechanisms on the adjustable components so they can be locked in place once set to a specific angle or length.

FIG. 3 shows the mirror support 10 with the mirror 19 in a first position. In this position, the first rod 17a of the adjustment member is angled upward, creating an acute angle between the first rod 17a and the top of the arms 13a, 13b. By angling the first rod upward, the joint 25 connecting the second rod 17b is located higher giving it a higher point of origin. This can be useful when the treatment provider is trying to look at the lower teeth or bottom portion of the mouth. The second rod 17b is at a right angle to the first rod 17a. Decreasing the distance between the mirror 19 and the mouth gives the user the ability to view an inside surface of the teeth due the more vertical angle of view. Lastly, the mirror 19 may be rotated towards the left arm 13a to direct the reflection to teeth on the left side of the patient's mouth. Accordingly, this position may be used when a user is trying to view the patient's lower left molars.

FIG. 4 shows the mirror support 10 with the mirror 19 in a second position. In this position, the first rod 17a is angled downward when compared to the first position discussed above. By angling the first rod 17a downward, the joint 25 connecting the second rod 17b is located lower and further away from the patient's mouth. This can be useful when the treatment provider is trying to look at the upper teeth or top portion of the mouth. The second rod 17b is angled upwards from the first rod 17a. This moves the mirror 19 closer to the patient's mouth to create a vertical viewing angle on the teeth. In this position, the mirror 19 is angled upward and not rotated. Accordingly, this position may be used when a user is trying to view the patient's upper incisors.

FIG. 1 shows the mirror support 10 in use on a patient's head. The arms 13a, 13b are secured around the patient's ears by the ear hooks 11a, 11b, and the cross-member 15 rests on the patient's chin. The projections 21 are positioned to keeps the edges of a dental dam secured away from the working area (the dental dam is not shown in Figures to emphasize the features of the mirror support 10). The mirror 19 and associated adjustment members 17a, 17b are adjusted to create a reflection of the patient's upper mouth for visualization and illumination. Since every portion of the mirror support 10 and dental dam (not shown) are connected to the patient's head, movement of the head will not cause the mirror 19 to require readjustment. In some cases, the treatment provider may want to turn the patient's head so that it is easier to access a specific tooth or because the provider is using a specialized tool. Other times, the patient may move from discomfort. Time can be saved during the operation by having the mirror 19 follow the patient's mouth to prevent or minimize readjustments. Additionally, stress on the treatment provider may be minimized, since he/she will not need to bend over to visualize different areas of the mouth.

Having the mirror adjustment member 17a, 17b originate at the patient's chin allows the mirror 19 to be spaced apart from the patient's mouth. This creates a large working space for treatment to be performed, which typically involves the use of instrument with long handles that requires large movements. Further, the mirror 19 will be less affected by water and debris that may splash out of the patient's mouth because of the remote location. Since the mirror 19 does not need to fit within the patient's mouth, a large mirror 19 can be used, which gives a comprehensive look at the patient's mouth. In some embodiments, the mirror 19 may have an anti-fog coating to prevent fogging caused by the patient's breathing.

A method of using the mirror support 10 may include adjusting the length of the arms 13a, 13b and cross-member 15 to fit the patient's face, and locating the cross-member 15 at a desired location for the treatment provider; fitting a dental dam around the portion of the mouth receiving the treatment; placing the mirror support 10 on the patient's face and readjusting its size, if necessary; connecting the peripheral portions of the dental dam to the projections 21 on the arms 13a, 13b and cross-member 15 so the dam is held taught and out of the way of the treatment provider; adjusting the adjustment arms 17a, 17b to position the mirror 19 at a location where it will produce a reflection of the portion of the patient's mouth receiving treatment; adjusting the angle of the mirror 19 by adjusting the joints 25 to produce a reflection of the portion of the mouth receiving treatment; readjusting the adjustment arm joints 25 and the mirror 19 to reflect other portions of the mouth or the same portion of the mouth from a different point of view; and removing the support 10 from the patient when the treatment is complete.

The ear-mounted dental mirror support 10 may be designed as a kit including multiple modular parts. For example, the kit may include multiple mirror sizes, shapes, and/or magnification levels. The kit may also include multiple adjustment members having varying amounts or rods, lengths of rods, and types of pivots. In addition, the kit may also include multiple types of arms with varying sizes and varying types of ear securement portions. The kit will allow a treatment provider to customize a device based on which component they prefer, or to customize a device for a specific procedure or patient.

It is to be understood that the ear-mounted dental mirror support is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. An ear-mounted dental mirror support, consisting of:
    a left arm and a right arm, each of the arms having a first end and an opposite second end, an ear securement portion on the first end, wherein each of the arms includes a plurality of projections for holding a dental dam, further wherein the plurality of projections on each of the arms extend parallel to each other and are disposed in a horizontal plane:
    a cross-member having a left end and a right end, the second end of the left arm being connected to the left end of the cross-member and the second end of the right arm being connected to the right end of the cross-member, wherein the cross-member includes a projection for holding a dental dam, wherein the projection extends in the horizontal plane so as to be coplanar with the plurality of projections;
    a set of projections being attached to the connection of the cross-member and the second respective ends of the left and right arms, wherein each projection of the set of projections extends perpendicular to the plurality of projections disposed in the horizontal plane;
    an adjustment member having a first end pivotally connected directly to a center of the cross-member and an opposite second end, wherein the adjustment member comprises at least two pivotally connected rods, wherein one of the at least two rods includes the first end and another of the at least two pivotally connected rods includes the opposite second end; and
    a mirror pivotally connected to the second end of the adjustment member.

2. The ear-mounted dental mirror support according to claim 1, wherein the pivotally connected rods comprise a ball joint.

3. The ear-mounted dental mirror support according to claim 1, wherein the ear securement portions comprise hooks configured to wrap around the back of a patient's ears.

4. The ear-mounted dental mirror support according to claim 1, wherein the cross-member consists of a straight rod.

* * * * *